United States Patent [19]

Amato et al.

[11] 4,036,985

[45] July 19, 1977

[54] MONO SUBSTITUTED MALONIC ACID DIAMIDES AND PROCESS OF PREPARING THEM

[76] Inventors: Jose Amato; Marta Propker; Magdalena Julia Beatriz Pongracz; Jorge Luis Jose Szabo, all of Humahuaca 4065, Buenos Aires, Argentina

[21] Appl. No.: 596,354

[22] Filed: July 16, 1975

[51] Int. Cl.$^2$ .......................................... C07C 103/44
[52] U.S. Cl. ............................... 424/320; 260/558 A; 260/561 A; 260/562 N; 424/324
[58] Field of Search .......... 260/558 A, 562 N, 561 A, 260/558 A; 424/324, 320

[56] References Cited

U.S. PATENT DOCUMENTS 3,758,574  9/1973  Melton et al. ................... 260/558 A

OTHER PUBLICATIONS

Buttini, et al., (I) Chem. Abst., 1962, column 8541.
Wagner, et al., Synthetic Organic Chem., Wiley, 1953, pp. 568-569.
Walker, et al., J. Chromatog 45 (1969), pp. 322-333.
Miyata, et al., Chem. Abst. 69, (1968), No. 43372.
Buttini, et al., (II) Chem. Abst. 69, (1968), No. 106663.

*Primary Examiner*—Arthur P. Demers
*Attorney, Agent, or Firm*—Karl W. Flocks

[57] ABSTRACT

The present invention relates to new 2-mono substituted malonic acid diamides. Furthermore, the invention relates to a process of preparing these compounds. Also the invention relates to a pharmaceutical composition including as an active antiinflammatory-analgesic-antipyretic agent compourd according to the invention and methods of treating with the new compounds and compositions, warm blooded animals.

9 Claims, 4 Drawing Figures

MONO SUBSTITUTED MALONIC ACID DIAMIDES AND PROCESS OF PREPARING THEM

DISCUSSION OF PRIOR ART

It has been well known through many years (Akt. Ges pat. Chem. Zentr. I, 299 (1906) and more recently: P. Görog, L. Sporny, y Vincze, Am. J. Hosp. Pharm. 22, 63 (1965); P. Görog, L. Sporny, Arzn. Forsch. 16, 1211 (1966), that different malonic acid amides have been pharmacologically assayed. Some of these compounds were found to be devoid of toxic action, but others were toxic.

BACKGROUND OF THE INVENTION

Field of the Invention

The present invention relates to 2-mono substituted malonic diamides, having the formula:

RHC (CONHR')$_2$ wherein R is an alkyl or aryl group and R' is an aromatic or N-dialkylamine alkyl radical.- Also, R, is an aralkyl group.

Some of these compounds show interesting pharmacological properties and low secondary effects.

As R substituents are preferred methyl, n-butyl, phenyl and benzyl groups.

As R' 3-dimethylaminopropyl radical is preferred.

A general process of preparing these new compounds comprises the conversion of the corresponding mono substituted malonic di lower alkyl esters into amides by heating the above esters with the corresponding amines. In the course of the reaction an alcohol is produced as by product and this alcohol is distilled off, and measured in order to determine the yield of the reaction. The final products are isolated by vacuum distillation, or by recrystallization of the reaction products from alcohol.

BRIEF DESCRIPTION OF THE DRAWINGS.

The drawings illustrate the diagrams of the IR spectrum of some of the new compounds.

Figure 1:
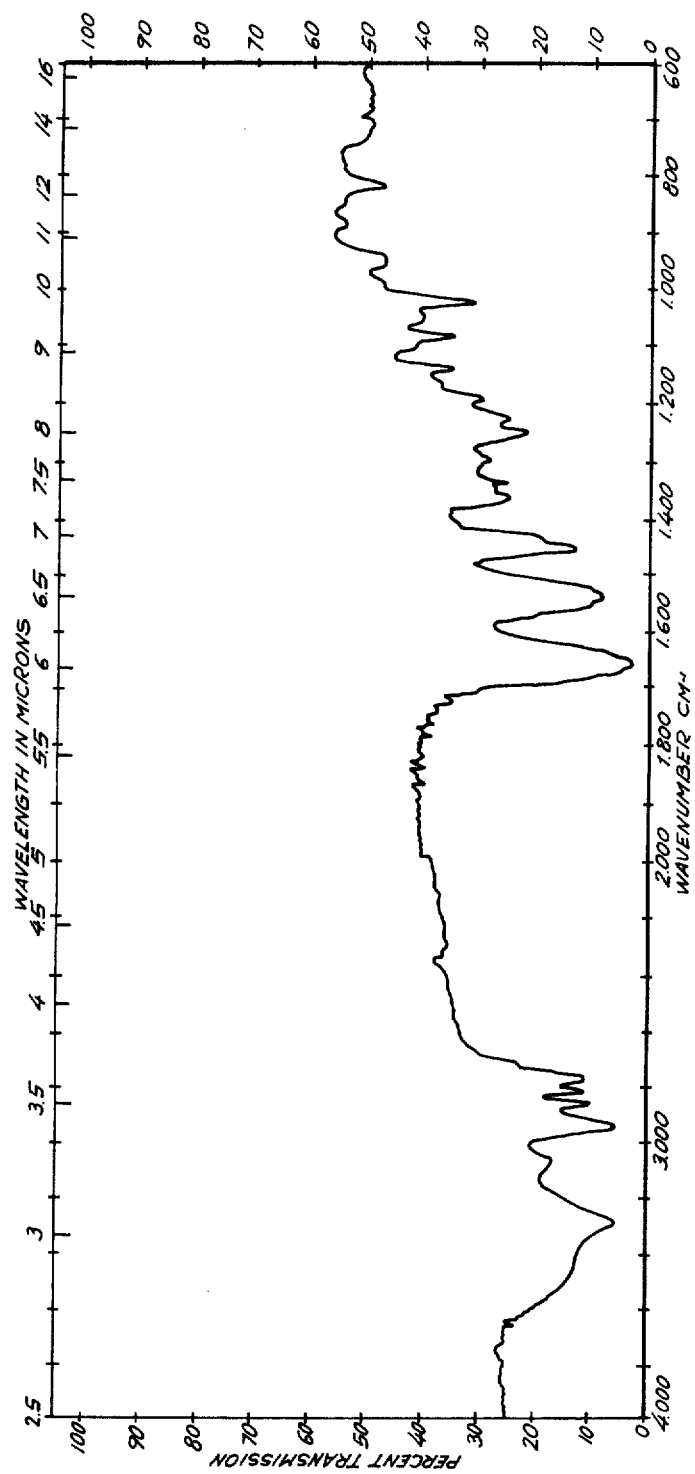
FIG. 1 corresponds to the compound illustrated by examples XVI.
Figure 2:
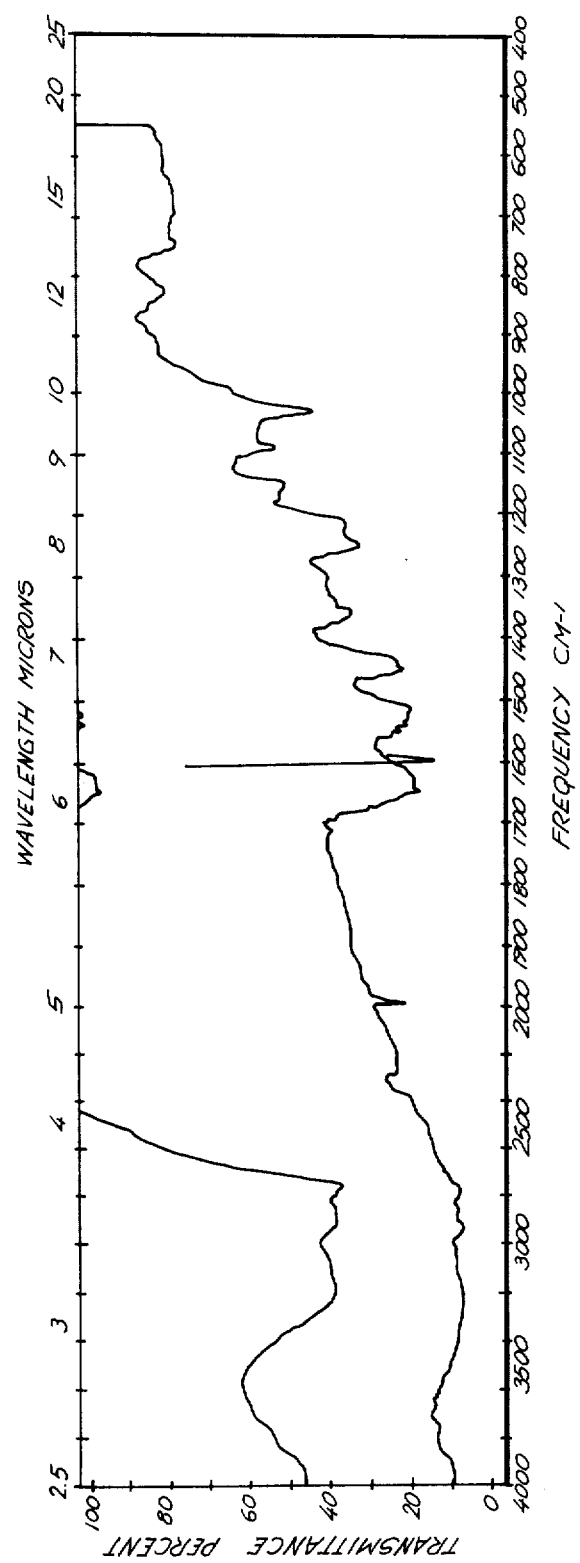
FIG. 2 to the compound illustrated by example XVII.
Figure 3:
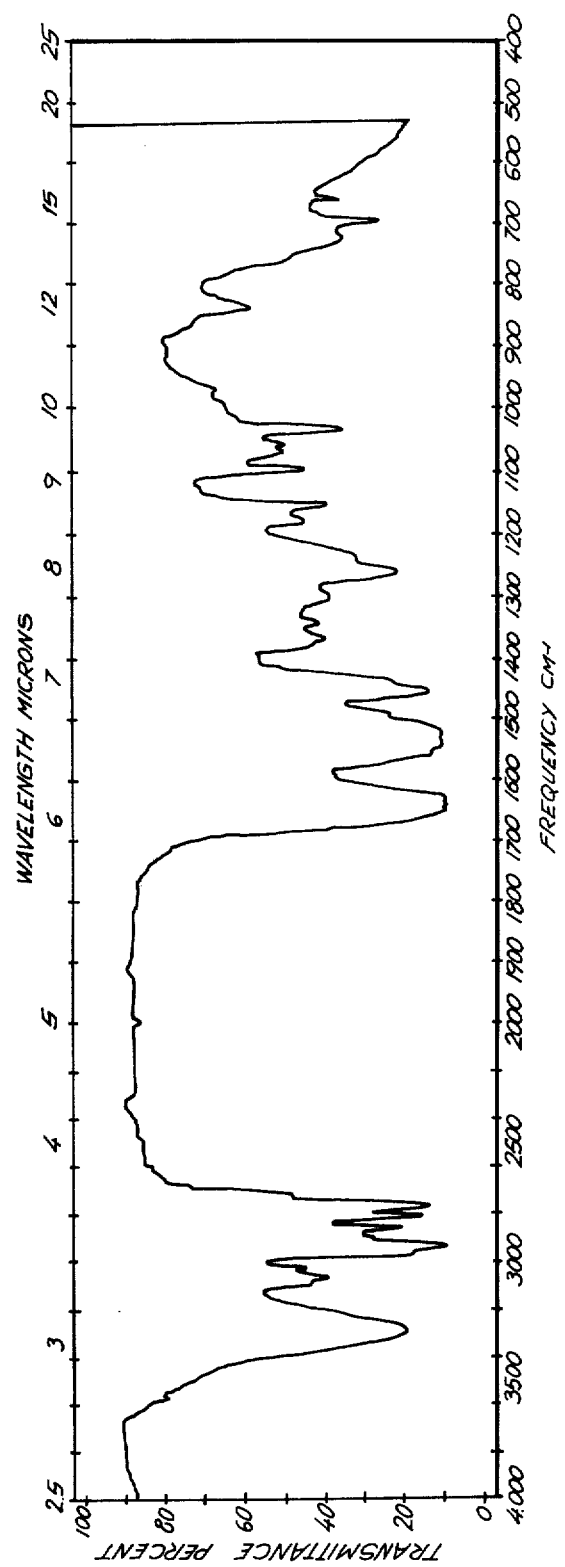
FIG. 3 to the compound illustrated by example XVIII and finally FIG. 4, to the compound illustrated by example XIX.
Figure 4:
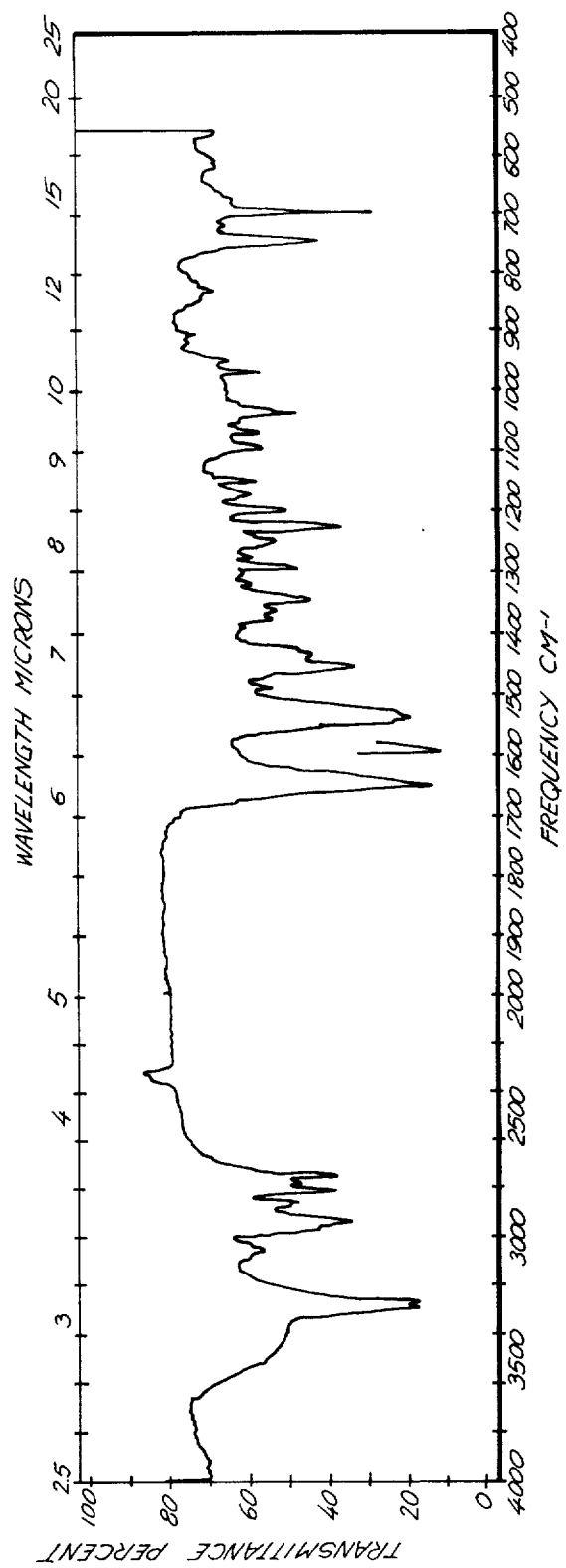

The following examples illustrates the invention but do not limit the same to the details set forth therein.

EXAMPLE I 2 n-butyl malonic acid N N'bis phenethylamide.

0,42 mole or β-phenyl ethyl amine are reacted with 0.20 mole of 2 n-butyl diethyl malonate and heated in an oil bath. It is necessary to have a slow distillation of the alcohol formed in the reaction through a short column in order to avoid the loss of reactants. When evolution of alcohol ceases (about 3-4 hours) it rises to 21 ml corresponding to a yield of 91%. The oil temperature is maintained around 180°-200° C.

Heating is stopped and the remainder product crystallizes as a mass when cooling. White crystals are obtained of a mp. 110° C (from alcohol).

EXAMPLE II 2-n-butyl malonic acid N N'bis (m-methyl) phenylamide

Following the procedure described in example I are used 0.42 mole of m-toluidine and 0.20 mole of n-butyl diethyl malonate, 20 ml of alcohol are slowly distilled corresponding to a yield of 89% is obtained. White crystals mp. 113° C (alcohol).

EXAMPLE III 2 n-butyl malonic acid N N'bis (p-methyl) anilide.

Following the procedure described in example I are used 0.42 mole of p-toluidine and 0.20 mole of n-butyl diethyl malonate. 12.5 ml of alcohol are distilled corresponding to a yield of 54%. The oil temperature of the bath must be 200°-215° C.

The product cyrstallizes from alcohol, mp. 194°-5° C.

EXAMPLE IV 2 n-butyl malonic acid N N'bis 2-6 xylidide.

Following the procedure described in example I are used 0.42 mole 2-6 xylidine and 0.20 mole 2 n-butyl diethyl malonate 14 ml of alcohol are distilled and corresponding to a yield of 60%. White crystals (from alcohol) mp. 280° C.

EXAMPLE V 2 n-butyl malonic acid N N'bis (p-ethyl) anilide.

Following the procedure described in example I, are used 0.42 mole of p-ethyl aniline and 0.20 mole of 2 n-butyl diethyl malonate. 17 ml of alcohol are distilled corresponding to a yield of 73%. White crystals (from alcohol) mp. 170° C.

EXAMPLE VI 2 n-butyl malonic acid N N'bis (o-methoxy) anilide

Following the procedure described in example I are used 0.42 mole o-anisidine and 0.20 mole 2 n-butyl diethyl malonate. 17 ml of alcohol are distilled corresponding to a yield of 73%. White crystals (from alcohol) mp. 138° C.

EXAMPLE VII 2 n-butyl malonic N N'bis (p-mehoxy anilide

Following the procedure described in example I are used 0.42 mole of p-anisidine and 0.20 mole 2 n-butyl diethyl malonate. 19 ml of alcohol, are distilled corresponding to a yield of 82%. White crystals (from alcohol) mp. 195°-6° C.

EXAMPLE VIII 2 n-butyl malonic acid N N'bis (o-ethoxy) anilide

Following the procedure described in example I, are used 0.42 mole o-phenetidine and 0.20 mole of 2 n-butyl diethyl malonate. 8.5 ml of alcohol are distilled, corresponding to a yield of 36%. The temperture of the bath was raised to 210°-220° C. The mixture is allowed to cool and crystallizes from ethyl alcohol. White crystals, mp. 110° C.

EXAMPLE IX 2 n-butyl malonic acid N N'bis (p-ethoxy) anilide

Following the procedure described in example I are used 0.42 mole p-phenetidine and 0.20 mole of 2 n-butyl diethyl malonate. 19.5 ml of alcohol, are distilled corresponding to a yield of 84%. The product crystallizes from alcohol M.p. 206.5° C.

EXAMPLE X 2 n-butyl malonic acid N N'bis (p-propoxy) anilide

Following the procedure described in example I are used 0.42 mole of p-propoxy aniline and 0.20 mole of n-butyl diethyl malonate. 7.5 ml of alcohol, are distilled corresponding to a yield of 32%. The oil temperature of the bath was raised to 240° C. Crystallization from alcohol afforded. White crystals mp. 194.5-5° C.

EXAMPLE XI 2 n-butyl malonic acid N N'bis (p-chloro) anilide

Following the procedure described in example I, are used 0.42 mole p-chlorophenyl amine and 0.20 mole 2 n-butyl diethyl malonate. c. a. 17 ml of alcohol, are distilled corresponding to a yield of 75%. The product has a mp. of 227° C (alcohol).

EXAMPLE XII 2 n-butyl malonic acid N N'bis 4 methylene pyridin diamide

Following the procedure described in example I, are used 0.42 mole 4 aminomethyl pyridine and 0.20 mole of 2 n-butyl diethyl malonate. 8 ml of alcohol are distilled, corresponding to a yield of ca 35%. Crude product was crystallized from alcoholwater 1: 2 p in vol. White needles mp. 156° C.

EXAMPLE XIII 2 methyl N N'bis (o-methoxy) phenyl malondiamide

Following the procedure described in example I, are used 0.42 mole of o-anisidine and 0.20 mole of 2-methyl diethyl malonate. 12 of alcohol are distilled, corresponding to a yield of 52%. mp. 162° C (from alcohol).

EXAMPLE XIV 2-phenyl N N'bis (o-methoxy) malondiamide

Following the procedure described in example I, are used 0.42 mole of o-anisidine and 0.20 mole of 2 phenyl diethyl malonate. 16 ml of alcohol are distilled, corresponding to a yield of ca 70%. mp. 142° C (from alcohol).

EXAMPLE XV 2-benzyl N N'bis (o-mothoxy phenyl) malondiamide

Following the procedure described in example I, are used 0.42 mole of a o-ansidine and 0.20 mole of 2-benzyl diethyl malonate. 13 ml of alcohol are distilled, corresponding to a yield of ca 57%. The product has a mp. 145° C (from alcohol).

EXAMPLE XVI 2 n-butyl N N'bis (3-dimethylamino propyl) malondiamide 0.42 mole of 3-dimethylamino propylamine and 0.20 mole of 2 n-butyl diethyl malonate are heated in an oil bath, and with the aid of a Vigreux column of 40 cm length 10 ml of liquid is distilled very slowly (8 hrs). The temperature of the vapors must not exceed 79° C. 20 ml of the amine are added, and 5 ml more of liquid are distilled in the same manner and then another 20 ml of liquid are distilled but more rapidly (excess of reactants). A total of 35 ml of liquid are so distilled. After vacuum distillation of a forerum 40 g. (60% yield) of product $bp_{1.5}$: 205°-10° C are obtained as a liquid, this crystallized as a mass mp. 42°-3° C. White product wax-like appearance are obtained.

EXAMPLE XVII 2-methyl N N'bis (3-dimethylamino propyl) malondiamide

Following the procedure described in example XVI are used 0.42 mole of 3-dimethylamino propylamine and 0.20 mole of 2-methyl diethyl malonate. The product was isolated after vacuum distallation of the forerum, by crystallization of the remainder material in alcohol. White crystals, mp. 58° C.

EXAMPLE XVIII 2-phenyl N N'bis (3-dimethylamino propyl) malondiamide

Following the procedure described in example XVI are used 0.42 mole of 3 dimethylamino propylamine and 0.20 mole of 2-phenyl diethyl malonate. The product was obtained after vacuum distillation of forerun as an oil, $bP_2$: 222°-6° C.

EXAMPLE XIX 2-benzyl N N'bis (3-dimethylaminopropyl) malondiamide

Following the procedure described in example XVI are used 0.42 mole of 3-dimethylamino propylamine and 0.20 mole of 2-benzyl diethyl malonate, the product is obtained after vacuum distillation of forerun, by crystallization of the remainder material in alcohol. White cristals, mp. 99° C.

Pharmacological screening

In order to determined the pharmacological properties of the new compounds, a battery of test units were used, which can give an idea about the future therapeutic application of the new compounds.

From all the substances some were selected which had an important therapeutic index.

According to their activity the substances can be classified in two groups:

1. Amide compounds which are obtained from aromatic amines. The substituent in position 2 of the malonic moiety is alkyl, phenyl or benzyl radical numbered from I to XV. This substances have some antiinflammatory, analgesic, antipyretic activity but, these are not statistically significant when comparing with commercial drugs, like benzidamine, indomethacin or phenylbutazone, although they have no toxicity and minimal side effects. According to their activity (ED 50) the compounds can be arranged by the sequence VIII > VI > III > IV > XI > II > I > VII > IX > X > V > XII > XV > XIII > XIV in decreasing activity in addition, compound I has a slight activity on central nervous system, studied by Dews P. method (Brit. J. Pharmacol. 8,46 (1953). It was also observed that compound I promote a slight decrease on rat's arterial pressure.

2. In the second group there are more effective substances in regard to their antiinflammatory, antipyretic, analgesic activity. They contain in their molecule the same malonic moiety of above mentioned group but, there are obtained from alkyl amines, selected from the class consisting in dimethylaminopropyl amine. This compounds, numbered from XVI to XIX, have an interesting pharmacologic activity when comparing with commerial drugs such as benzidamine, indomethacin and phenylbutazone. As an example of this group of compounds numbered XVI was selected whose pharmacological screening was as follows:

A. Antiinflammatory activity:
A.1.Carrageenin test (Winter C.A., et al. International Symposium on non-steroidal Antiinflammatory drugs, September 1974, Milan, Excepta Medica Foundation) ED 50:10 mg/Kg., i.p.: 40 mg/Kg p.os.
A.2.Dextran Test: Courvoisier S., Ducrot R. Vandernissen L., Arch. Int. Pharmacodyn. 99, 974 (1954).
A.3.Arthritis induced by Freund's Adjuvant (Winter C.A. Nuss G.W. Arthristis Rheum. 9, 394 (1966) ED 50:40 mg/KG p.os.
A.4.Evans-Blue-Carrageenen Induced Pleural Effusion (Toxicol. and Appl. Pharm. 26, 575 (1973) ED 50:50 mg/Kg p.os.
A.5.Local Antiinflammatory action: (Tonelli G., Thibault L., Ringler I.- J.Endocr. 77, 625 (1963) ED 50:1%.
A.6.Randall-Selitto Test: (Arch. Int. Pharmocodyn. 111, 409 (1957) ED: (80 mg/kg p.os.)

B. Analgesic activity
B.1.Writting test (Witking et al J. Pharmacol. Exp. Therap. 133,400 (1961) ED 50:5 mg/Kg i.p. 100 mg/Kg p.os.
C. Antipyretic Activity: (Teotino V.N.; Friz L.P., Gandini A. and Della Bella D.-Med. Chem. 6, 248 (1963). ED 50: 15 mg/Kg l.p. 100 mg/kg. p.os.
D. Pharmacological Complementary Screening:Compound XVI has no antihistaminic, antiserotoninic nor antibradykinine effect. Compound XVI has no curare like activity when comparing with gallamine. (Vaney, Linegar, Holadoy (1948). Compound XVI does not modify CNS in treated mice nor arterial pressure.

Toxicological studies.

a. Acute toxicity of the substances was determined.- Lethal dose 50 was assayed in Wistar rats by oral and intraperitoneal route using Lichtfield and Wilcoxon test (Bibl. J. Pharm. and Exp. Ther. 96, 99 (1949). LD 50 of this compounds can be assumed as XIX < XVI < XVIII < XVII.

b. Neuropharmacological Irwin's test (Science 136, 123 (1962) was also studied.

c. Reference compounds were administered daily during 90 days (subacute toxicity) by oral route. Histopathological examination of different organs and biochemical analysis of blood such as glycaemia, uremia and haemogram, were performed. Rats, mice and guinea-pigs were used. No abnormalities were found with compound XVI in all the studied species.

d. Oral chronic toxicity was studied, aministering this compound daily, during 12 months. Weight increase and behaviour was controlled during this period. After treatment macroscopical examination of organs and biochemical study of blood like glycaemia, uremia and haemogram was performed. No abnormalities were found when comparing with control groups of animals treated with saline.

Teratological studies

Possible structural and functional abnormalities which could arise during gestation were studied on different species, and following the litters up to the third generation. References compounds were orally administered at their effective does, during pregnancy. It was determined litter-size, weight of foeti and number of resorptions of the offspring. No abnormalities were found when comparing with control groups treated with saline in the same conditions.

Side effects

Gastrointestinal lesions: The effect on the gastric mucosa was studied acording to Roberts, (Proc. Soc. Exptl. Biol. Med. 99, 443 (1958). Drugs were administered orally by stomach tube during 5 days and after the treatment, the animals were killed, the stomachs dissected and the mucosa examined for possible hemorrhages haemorrages. Duodenal ulcers were also studied for. Compound XVI have minimal effect, on gastric mucosa.

Pharmacological conclusions

According to their therapeutic index, a great range security was observed in compounds synthetized by us. The more important antiinflammatory, analgesic and anpyretic effect was observed in the group of mono substituted malonic bis (dimethylamino propyl) diamides. The pharmacological activity shows that compound XVI is more active than phenylbutazone and has similar performance than indomethacin. It is note worthy its low side-effect respect of the gastrointestinal lesion. Longterm administration does not produce toxic effects.

I claim:

1. New 2-monosubstituted malonic acid diamides of the formula

wherein R is a member of the group consisting of phenyl, benzyl, and lower alkyl of 1–4 carbons.

2. A compound according to claim 1 which is the 2-n-butyl N,N'bis (3-dimethylaminopropyl) malondiamide.

3. A compound according to claim 1 which is the 2-methyl N,N'bis (3-dimethylaminopropyl) malondiamide.

4. A compound according to claim 1 which is the 2-phenyl N,N'bis (3-dimethylaminopropyl) malondiamide.

5. A compound according to claim 1 which is the 2-benzyl N,N'bis (3-dimethylaminopropyl) malondiamide.

6. A process of preparing a compound according to claim 1 comprising the steps of:
   a. direct heating of the corresponding substituted malonic ester with 3-N, N'bis dimethylaminopropyl amine;
   b. slowly distilling off the alcohol formed in the reaction through a short column in order to avoid loss of reactants;
   c. measuring the amount of alcohol distilled to determine the yield of the reaction and control the course of the reaction; and
   d. isolating the final product by vacuum or by recrystallization.

7. A pharmaceutical composition comprising as an active anti-inflammatory, analgesic, anti-pyretic agent, an effect amount for said purpose of at least on compound of the formula

wherein R is a member of the group consisting of lower alkyl of 1–4 carbons, phenyl and benzyl, and a pharmaceutical carrier therefor.

8. A method of treating warm blooded organisms which comprises administering as an active antiinflamatory analgesic-antipyretic agent, at least one compound according to claim 1.

9. A method of treating warm blooded organisms, wherein a composition according to claim 7 is administered.

* * * * *